US011361418B2

United States Patent
Yuan et al.

(10) Patent No.: US 11,361,418 B2
(45) Date of Patent: Jun. 14, 2022

(54) TRANSFER LEARNING BASED CAPSULE ENDOSCOPIC IMAGES CLASSIFICATION SYSTEM AND METHOD THEREOF

(71) Applicant: ANKON TECHNOLOGIES CO., LTD, Wuhan (CN)

(72) Inventors: Wenjin Yuan, Wuhan (CN); Hao Zhang, Wuhan (CN); Hang Zhang, Wuhan (CN)

(73) Assignee: ANKON TECHNOLOGIES CO., LTD, Wuhan (CN)

( * ) Notice: Subject to any disclaimer, the term of this patent is extended or adjusted under 35 U.S.C. 154(b) by 267 days.

(21) Appl. No.: 16/810,812

(22) Filed: Mar. 5, 2020

(65) Prior Publication Data

US 2020/0286219 A1  Sep. 10, 2020

(30) Foreign Application Priority Data

Mar. 5, 2019  (CN) .......................... 201910165108.9

(51) Int. Cl.
*G06K 9/00* (2022.01)
*G06T 7/00* (2017.01)
(Continued)

(52) U.S. Cl.
CPC ........... *G06T 7/0002* (2013.01); *G06N 20/00* (2019.01); *G06T 7/215* (2017.01); *G06T 7/248* (2017.01);
(Continued)

(58) Field of Classification Search
CPC ......... G06T 2207/10068; G06T 7/0012; G06T 2207/30028; G06T 2207/10016;
(Continued)

(56) References Cited

U.S. PATENT DOCUMENTS

| 8,682,142 B1* | 3/2014 | Boskovitz | ............ G11B 27/034 386/278 |
| 2007/0053557 A1* | 3/2007 | Cahill | ................... G06T 7/0012 382/128 |

(Continued)

FOREIGN PATENT DOCUMENTS

CN  107240091 A  10/2017

OTHER PUBLICATIONS

Sun et al., "Removal of Non-informative Frames for Wireless Capsule Endoscopy Video Segmentation", 2012, Proceeding of the IEEE International Conference on Automation and Logistics Zhengzhou, China, Aug. 2012, pp. 294-299.*

(Continued)

*Primary Examiner* — Guillermo M Rivera-Martinez
(74) *Attorney, Agent, or Firm* — Treasure IP Group, LLC (57) ABSTRACT

The present invention provides a transfer learning based capsule endoscopic images classification system. The system removes the capsule endoscopic images with an average brightness value beyond the preset threshold, and removes the capsule endoscopic images without details based on image brightness standard deviation and image brightness gradient. The system also removes similar images from the capsule endoscopic images using optical flow method, classifies the capsule endoscopic images according to the corresponding anatomical structure, and obtains the classified capsule endoscopic images list arranged in chronological order. The system further determines and labels the position of the first image of each specific anatomical structure in the classified capsule endoscopic images list arranged in chronological order.

17 Claims, 3 Drawing Sheets

(51) Int. Cl.
*G06T 7/215* (2017.01)
*G06T 7/246* (2017.01)
*G06T 7/44* (2017.01)
*G16H 30/40* (2018.01)
*G06N 20/00* (2019.01)
*G16H 30/20* (2018.01)

(52) U.S. Cl.
CPC ............... *G06T 7/44* (2017.01); *G16H 30/20* (2018.01); *G16H 30/40* (2018.01); *G06T 2207/10068* (2013.01); *G06T 2207/30028* (2013.01)

(58) Field of Classification Search
CPC ........... G06T 2207/10024; G06T 7/174; G06T 2207/30092; G06T 7/90; G06T 2207/30004; G06K 9/6267
See application file for complete search history.

(56) References Cited

U.S. PATENT DOCUMENTS

| | | | | |
|---|---|---|---|---|
| 2011/0069876 | A1* | 3/2011 | Kanda | A61B 1/00052 382/134 |
| 2011/0135170 | A1* | 6/2011 | Wang | H04N 19/14 382/128 |
| 2012/0316421 | A1* | 12/2012 | Kumar | A61B 1/041 600/407 |
| 2013/0002842 | A1* | 1/2013 | Das | H04N 7/18 348/65 |
| 2013/0109915 | A1* | 5/2013 | Krupnik | G06F 3/0482 600/109 |
| 2016/0037082 | A1* | 2/2016 | Wang | G06T 5/006 348/65 |
| 2016/0292875 | A1* | 10/2016 | Kono | G06T 7/64 |
| 2018/0047165 | A1* | 2/2018 | Sato | A61B 1/00032 |
| 2018/0253839 | A1* | 9/2018 | Zur | G06T 7/0012 |
| 2018/0308235 | A1* | 10/2018 | Yuan | G06T 7/0014 |

OTHER PUBLICATIONS

Lee et al., "Reducing redundancy in wireless capsule endoscopy videos", 2013, Computers in Biology and Medicine 43 (2013), pp. 670-682.*

"Gastrointestinal Bleeding Detection in Wireless Capsule Endoscopy Images Using Handcrafted and CNN Feature". 2017 39th Annual International Conference of the IEEE Engineering in Medicine and Biology Society, Sep. 14, 2017. Abstract and Figure 2.

Exploring Transfer Learning for Gastrointestinal Bleeding Detection on Small-size Imbalanced Endoscopy Images, Xiuli Li. 2017 39th Annual International Conference of the IEEE Engineering in Medicine and Biology Society, Sep. 17, 2017. Abstract, Figure 2.

* cited by examiner

TRANSFER LEARNING BASED CAPSULE ENDOSCOPIC IMAGES CLASSIFICATION SYSTEM AND METHOD THEREOF

CROSS-REFERENCE OF RELATED APPLICATIONS

The application claims priority to Chinese Patent Application No. 201910165108.9 filed on Mar. 5, 2019, the contents of which are incorporated by reference herein.

FIELD OF INVENTION

The present invention relates to image processing technology, and more particularly to a transfer learning based capsule endoscopic images classification system and method thereof.

BACKGROUND

Existing capsule endoscope can take a large number of images (about 50,000 images) in a single examination, but among them, there are only small proportion of images of specific anatomical structure (such as cardia, pylorus, duodenum, etc.). It is quite difficult to pick out the required images from a large amount of data, which makes physicians' work more demanding. Therefore, there is a need for a method capable of removing redundant images and classifying the images according to specific anatomical structure of digestive tract, and thereby facilitating the work of physicians and improving their work efficiency.

SUMMARY OF THE INVENTION

The present invention provides a transfer learning based capsule endoscopic images classification system and a method thereof. The invention can quickly remove redundant images and eliminate the images without details to reduce the number of images that a physician needs to review and reduce the workload of the physician, and can quickly locate the images to various regions of digestive tract, improving work efficiency of the physician.

A system for transfer learning based capsule endoscopic images classification disclosed herein comprises an image preprocessing module, a similar image removal module, an image classification module, and a key image positioning module.

The image preprocessing module removes the capsule endoscopic images with an average brightness value beyond a preset threshold, and removes the capsule endoscopic images without details by using an image brightness standard deviation and an image brightness gradient.

The similar image removal module removes similar images from the capsule endoscopic images using optical flow method.

The image classification module classifies the capsule endoscopic images according to corresponding anatomical structure to obtain the classified capsule endoscopic images list arranged in chronological order.

The key image positioning module determines and labels the position of the first image of each specific anatomical structure in the classified capsule endoscopic images list arranged in chronological order.

Further, the image preprocessing module calculates an average brightness value M in the effective area of a capsule endoscopic image. When the average brightness value M is less than the too dark threshold Low, the image preprocessing module determines the corresponding capsule endoscopic image as too dark and removes the image. When the average brightness value M is greater than the too bright threshold High, the image preprocessing module determines the corresponding capsule endoscopic image as too bright and removes the image.

Further, the image preprocessing module calculates an image brightness standard deviation S and an image brightness gradient G in the effective area of a capsule endoscopic image, and counts the number of pixels B as the image brightness gradient G meets requirements. When the image brightness standard deviation S is less than the image brightness standard deviation threshold StdStd or the number of pixels B is less than the threshold for an effective gradient GradNum, the image preprocessing module determines that the corresponding capsule endoscopic image has no details and removes it.

Further, the similar image removal module removes similar images from the capsule endoscopic images using optical flow method, comprising:

setting K feature points in the effective area of the current capsule endoscopic image;

adjusting the brightness of next capsule endoscopic image, until the average brightness value of the next capsule endoscopic image as the same as the average brightness value of the current capsule endoscopic image;

in the effective area of the said next capsule endoscope image, setting the positions of feature points of the current capsule endoscopic image as initial positions, and searching for the best matching position of each feature point in the current capsule endoscopic image around the initial positions using optical flow method;

assigning a weight to the best matching position of each feature point, calculating the sum of weights of the best matching positions of all feature points as the image matching weight W, and removing similar images using the image matching weight W.

Further, the image classification module comprises a preset image data model module, a transfer learning model module and a manual feature extraction module.

The capsule endoscopic images processed by the image preprocessing module and the similar image removal module are processed by the preset image data model module to obtain a first image data feature. The first image data feature is processed by the transfer learning model module to obtain a second image data feature, and at the same time processed by the manual feature extraction module to obtain a third image data feature. The second image data feature and the third image data feature are fused to obtain an image classification data feature. According to specific anatomical structure, the capsule endoscopic images are classified by the image classification data feature.

Further, the key image positioning module removes interference data from the classified capsule endoscopic images arranged in chronological order by filtering, and then searches for the position of the first image of each anatomical structure in filtered capsule endoscopic images list.

A method for transfer learning based capsule endoscopic images classification, comprising:

removing the capsule endoscopic images with an average brightness value beyond the preset threshold, and removing the capsule endoscopic images without details based on the image brightness standard deviation and image brightness gradient;

removing similar images from the capsule endoscopic images using optical flow method;

classifying the capsule endoscopic images according to the corresponding anatomical structure to obtain the classified capsule endoscopic images list arranged in chronological order;

determining and labeling the position of the first image of each specific anatomical structure in the classified capsule endoscopic images list arranged in chronological order.

The present invention has the following beneficial effects.

The present invention removes too bright and too dark images according to the comparison of average brightness values and preset image brightness threshold, and removes images without details (the capsule endoscopic images of specific anatomical structures are rich in details) using image brightness standard deviation and image brightness gradient, which greatly reduces the number of images that need to be classified and improves classification efficiency.

The present invention realizes perfect removal of similar images using optical flow method, which reduces the number of images that need to be classified and improves classification efficiency.

The present invention greatly improves the image classification effect by combining artificial features and the features obtained by deep learning.

Elements in the figures are: 1. Image preprocessing module 1, 2. Similar image removal module 2, 3. Image classification module 3, 4. Key image positioning module 4.

DETAILED DESCRIPTION

The present invention is described in detail below with reference to the accompanying drawings and preferred embodiments.

Figure 1:
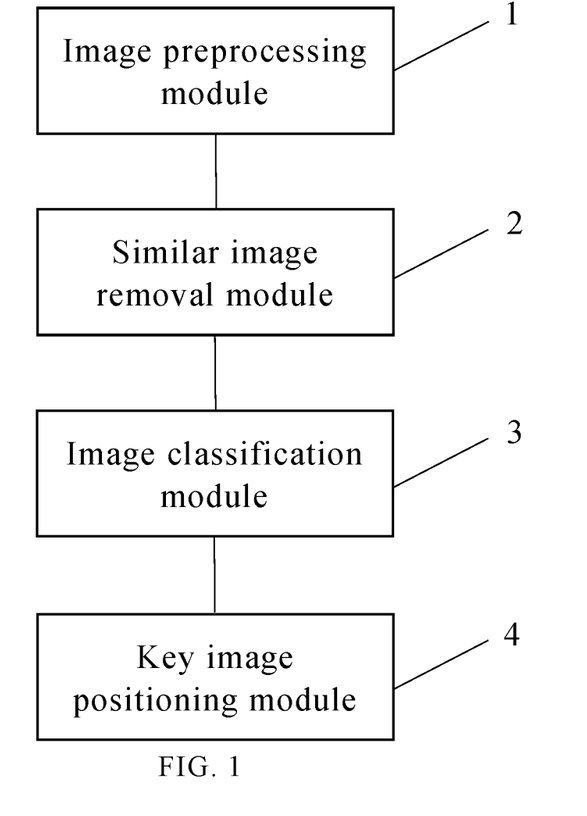
FIG. 1 is a structural view of the capsule endoscopic images classification system of the present invention.

The present invention provides a transfer learning based capsule endoscopic images classification system. As shown in FIG. 1, the capsule endoscopic images classification system comprises an image preprocessing module 1, a similar image removal module 2, an image classification module 3, and a key image positioning module 4. The image preprocessing module 1 compares the average brightness value with preset image brightness threshold in the effective area of each capsule endoscopic image, and removes excessively bright and dark images with the average brightness value beyond the preset image brightness threshold. The image preprocessing module 1 further calculates an image brightness standard deviation and an image brightness gradient in the effective area of each capsule endoscopic image, and removes the images without details (the capsule endoscopic images of specific anatomical structures are rich in details) using the image brightness standard deviation and image brightness gradient. The similar image removal module 2 i removes similar images from the pre-processed capsule endoscopic images using optical flow method which can overcome the adverse effects caused by image rotation, and adjusts image brightness to overcome the adverse effects caused by light. The image classification module 3 classifies the capsule endoscopic images processed by the image preprocessing module 1 and the similar image removal module 2 according to the corresponding anatomical structure, and obtains the classified capsule endoscopic images list arranged in chronological order. The key image positioning module 4 determines and labels the position of the first image of each specific anatomical structure in the classified capsule endoscopic images list arranged in chronological order.

Figure 2:
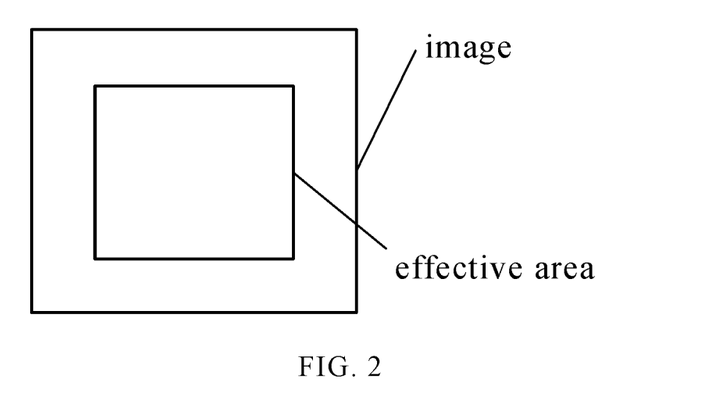
FIG. 2 is a structural view of an effective area of an image according to the present invention.

The effective area refers to an area at the center of the image. The shape of the effective area can be adjusted according to the image taken by the capsule endoscope, and the shape can be rectangular, circular, elliptical, or polygonal, etc. The size of the effective area can be adjusted according to the image taken by the capsule endoscope. When the area size exceeds the image size, the original image is used. Generally, the size of the effective area is ($\alpha \times$Width)$\times$($\alpha \times$Height), where, respectively, Width and Height are the width and height of image, and $\alpha$ is the area size coefficient, of which the value range is: $\alpha$=[0.2,1]. In the preferred embodiment, the shape of the effective area is rectangular, $\alpha$=0.7, as shown in FIG. 2.

Due to the complex environment of digestive tract, especially in the stomach which has a large cavity, during capsule endoscopy, a plurality of too bright and too dark images can be obtained, and at the same time, a plurality of smooth gastric wall images can be obtained. The smooth gastric wall images include no useful information, but greatly increase the number of images and affect the processing of capsule endoscopic images. The image preprocessing module 1 pre-processes the digestive tract images taken by the capsule endoscope, removes too bright and dark images, and removes the images without details. Specifically, the image preprocessing module 1 calculates an average brightness value in the effective area of each capsule endoscopic image, and remove too bright and too dark images using a preset image brightness threshold.

Specifically, the average brightness value M is calculated by the following formula:

$$M = \frac{\sum_{i}^{N} I_i}{N}.$$

Wherein, N is the number of image pixels in the effective area, $I_i$ is the gray value of the i-th pixel in the effective area.

When M<Low, the image preprocessing module determines that the brightness of the corresponding capsule endoscopic image is too dark, and removes it. When M>High, the image preprocessing module determines that the brightness of the corresponding capsule endoscopic image is too bright, and removes it.

Wherein, Low is the image too dark threshold, High is the image too bright threshold, which are both obtained through calculation of the brightness of actual images. Generally, the value range of the image too dark threshold Low is: Low=[30,80], and the value range of the image too bright threshold High is: High=[180,240]. In the preferred embodiment, Low=50, High=220.

The image preprocessing module 1 further calculates an image brightness standard deviation and an image brightness gradient within the effective area of each capsule endoscopic image, and removes the images without details according to the image brightness standard deviation and image brightness gradient.

Specifically, the image brightness standard deviation S is calculated by the following formula:

$$S = \sqrt[2]{\frac{\sum_i^N (I_i - M)^2}{N}}.$$

Wherein, N is the number of image pixels in the effective area, $I_i$ is the gray value of the i-th pixel in the effective area, M is the average brightness value.

The specific method that the image preprocessing module 1 uses to remove the images without details, comprises following steps.

First, sobel operator is used to obtain the brightness gradients $f_x$ and $f_y$ in the horizontal and vertical directions. The brightness gradient is $G=f_x^2+f_y^2$.

Then, the number of pixels B as the image brightness gradient G meets requirements is counted by the following formulas:

$$B = \sum_i^N Sg(G_i), \quad Sg(G_i) = \begin{cases} 1, & G_i \geq Grad \\ 0, & else \end{cases}.$$

When S<Std or B<GradNum, the image preprocessing module determines that the corresponding capsule endoscopic image has no details and removes it.

Wherein, $G_i$ is the gradient of the i-th pixel in the effective area, S is the brightness standard deviation in the effective area of the capsule endoscopic image, N is the number of image pixels in the effective area, Grad is the threshold for determining if the image gradient is effective, Std is the image brightness standard deviation threshold, and Grad-Num is the threshold for the number of effective gradients.

When the gradient $G_i$ of the i-th pixel in the effective area exceeds Grad, it is considered to be an effective brightness gradient. Generally, the value range of Grad is: Grad=[10, 5000]. In the preferred embodiment, Grad=1100.

In addition, generally, the value range of Std is: Std=[0, 100], and the value range of GradNum is: GradNum=[10, 1000]. In the preferred embodiment, Std=20, Grad-Num=300.

For a specific anatomical structure, the capsule endoscope can continuously take a plurality of images, resulting in image redundancy and affecting the image review efficiency of physicians. The similar image removal module 2 can remove these redundant images, and thereby improve the work efficiency of physicians. An optical flow method is used to remove similar images. The optical flow method can overcome the adverse effects caused by image rotation, and adjust the image brightness to overcome the adverse effects caused by light, which has a good effect.

Figure 3:
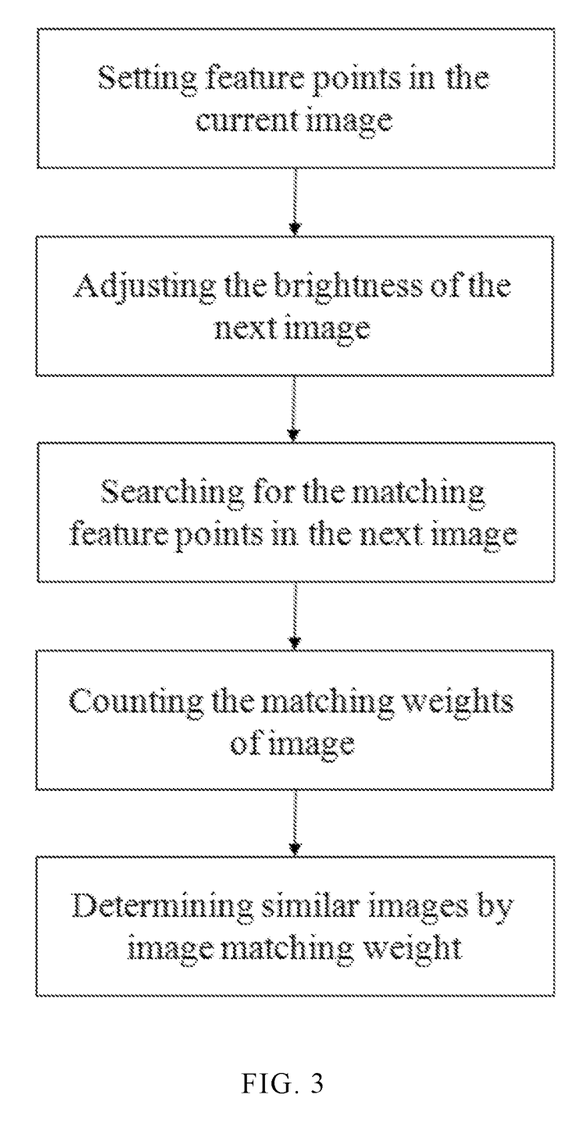
FIG. 3 is a flowchart determining similar images using an optical flow method according to the present invention.

Referring to FIG. 3, a flowchart determining similar images using an optical flow method, the specific steps are as follows.

Step S21, K feature points are set in the effective area of the current capsule endoscopic image.

Step S22, the brightness of next capsule endoscopic image is adjusted, and the average brightness value of next capsule endoscopic image is adjust as the same as the average brightness value of the current capsule endoscopic image, so as to reduce the influence of light. The specific image brightness adjustment method is: $I_{next}=I_{next}-M_{next}+M_{current}$ wherein, $I_{next}$ is the gray value of all pixels of the next image, $M_{next}$ is the average brightness value of the next image, and $M_{current}$ is the average brightness value of the current image.

Step S23, in the effective area of the said next capsule endoscopic image, the positions of feature points of the current capsule endoscopic image are set as initial positions, and search for the best matching position of each feature point in the current capsule endoscopic image around the initial positions using the optical flow method.

Step S24, a weight is assigned to the best matching position of each feature point, the sum of weights of the best matching positions of all feature points is calculated as the image matching weight, and similar images are removed using the image matching weight.

Figure 4:
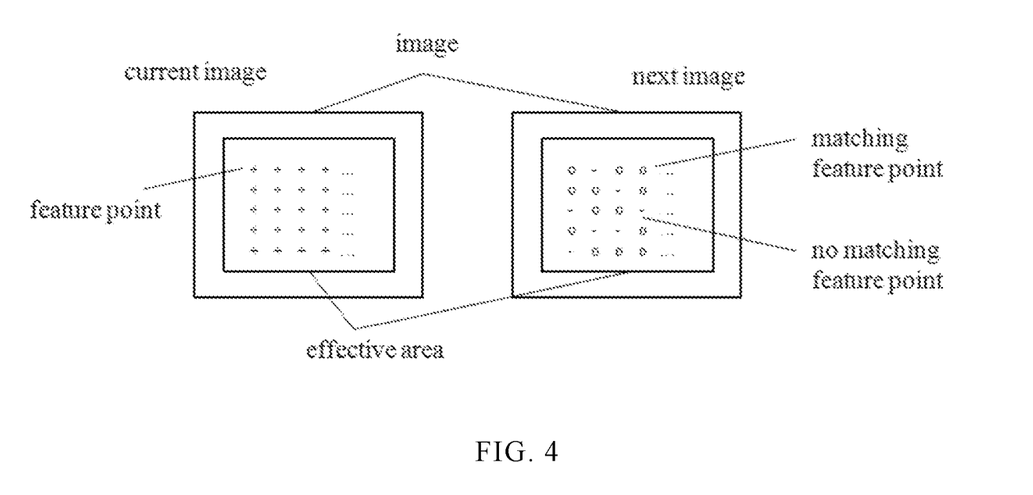
FIG. 4 is a schematic view of feature points matching using an optical flow method according to the present invention.

Due to the characteristics of capsule endoscopic images, few feature points can be obtained using sift method. In order to overcome this shortcoming, the step S21 can uniformly set K feature points in the effective area of the current capsule endoscopic image, as shown in FIG. 4. Generally, K=[9, 2500]. In the preferred embodiment, K=100.

Further, in order to eliminate the influence of flat area on the image matching weight, the weights of feature points at the image details is adjusted. In the step S24, the specific method for determining similar images by using the image matching weight comprises following steps.

First, the image matching weight W is calculated by the following formula:

$$W = \sum_i^P Sg(S_i), \quad Sg(S_i) = \begin{cases} u, & S_i > Astd \\ v, & else \end{cases}.$$

Wherein, P is the number of matched feature points, $S_i$ is the image brightness standard deviation in the neighborhood (Asize×Asize) of the i-th feature point of the current image (for calculation method, refer to that of the image brightness standard deviation S in the image preprocessing module 1), AStd is a threshold for determining the existence of details in the neighborhood (Asize×Asize), and Asize is the size of neighborhood. Generally, Asize=[3,21], AStd=[1,10]. In the preferred embodiment, Asize=9, AStd=5.

Then, whether they are details in the neighborhood of image feature point is determined. When $S_i$>AStd, it is determined that the neighborhood of the i-th feature point has details, the matching weight of the i-th feature point is u; otherwise, the matching weight of the i-th feature point is v. Generally, u=[2,20], v=[0,2]. In the preferred embodiment, u=10, v=1.

Finally, whether the images are similar is determined. When the image matching weight W<Wth or P<Pth, it is determined that the corresponding capsule endoscopic images are not similar. Otherwise, it is determined that the corresponding capsule endoscopic images are similar. Wherein, Pth is the threshold of the number of matched feature points, Wth is the image matching weight threshold. Generally, Wth=[0,K×u], Pth=[0,K]. In the preferred embodiment, the image matching weight threshold Wth=70, and the threshold of the number of matched feature points Pth=30.

It can be seen that the more details the neighborhood of an image feature point has, the higher the matching weight of the feature points is; otherwise, the matching weight is lower. The higher the image matching weight W, the more similar the corresponding capsule endoscopic images; otherwise, they are less similar. The larger the number of matched feature points P, the more similar the corresponding capsule endoscopic images; otherwise, they are less similar.

Figure 5:
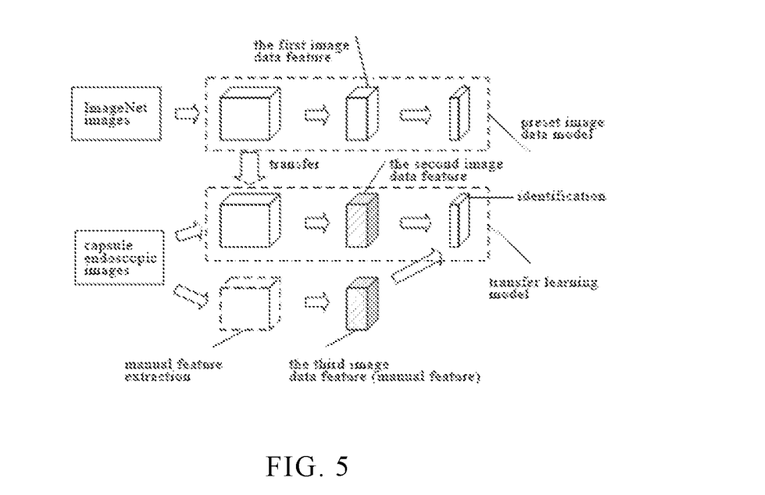
FIG. 5 is a flowchart of transfer learning according to the present invention.

Referring to FIG. 5, a flowchart of digestive tract images classification performed by the image classification module 3 using transfer learning. The image classification module 3 comprises a preset image data model module, a transfer learning model module, and a manual feature extraction module. The specific steps of the image classification module 3 in classifying the capsule endoscopic images processed by the image preprocessing module 1 and the similar image removal module 2 are as follows.

Step S31, first image data features are extracted from the preset image data model module.

Step S32, features are extracted using the transfer learning model module from the first image data features to obtain second image data features.

Step S33, third image data features are manually extracted from the capsule endoscopic images using the manual feature extraction module. The third image data features include features such as image color, texture, and gradient.

Step S34, the second image data features and the third image data features are fused to obtain image classification data features, and the image data classification features are classified according to specific anatomical structure.

The steps S31, S32 and S33 are performed simultaneously.

The preset image data model can be a model that has been trained in other fields, such as a model that works well in the natural image field, a model that is well classified in other medical image fields, etc. In the preferred embodiment, the preset image data model is the model inception-v3 that works well on natural images.

In the step S31, the parameters of the first image data feature can be completely trained for adjustment, partially trained for adjustment, or not adjusted. In the preferred embodiment, the parameters of the first image data feature are not adjusted.

In the step S32, the second image data feature can be adjusted according to the situations, by adjusting model convolution sum and parameters, increasing or reducing convolution layers, while adjusting the fully connected layers. In the preferred embodiment, the second image data feature comes with an increase of one convolution layer and an adjustment of fully connected parameters.

In the step S33, the color, texture and gradient features of the capsule endoscopic images are extracted manually, and the color feature is obtained by calculating the Hu matrix of each channel of HSV.

The texture feature is a CLBP (Completed Local Binary Pattern) histogram, which includes symbol CLBP_S and margin CLBP_M. The specific calculation method is:

$$CLBP\_S_{L,R} = \sum_{l=0}^{L-1} s(g_l - g_c)2^l, \quad s(x) = \begin{cases} 1, & x \geq 0 \\ 0, & x < 0 \end{cases}$$

$$CLBP\_M_{L,R} = \sum_{l=0}^{L-1} t(V_l, c)2^l, \quad t(x, c) = \begin{cases} 1, & x \geq c \\ 0, & x < c \end{cases}$$

Wherein, $2^l$ represents the weight of current pixel, s is a compare operation, s(x) determines whether the gray difference x>0, t(x, c) determines whether the gray difference x>threshold c, L is the number of pixels to be used in the neighborhood where the current pixel radius is R, $g_c$ is the value of G (green) channel minus B (blue) channel of the current pixel to be processed, $g_l$ is the value of G channel minus B channel of the pixels around the current pixel, the position of $g_l$ is (R cos(2 πl/L), R sin(2πl/L)), $V_l=|g_l-g_c|$ is the absolute value of the difference between the current pixel and the neighboring pixel, the threshold c is an average value in the effective area $V_l$.

In the step S34, the fusion of image data features, such as fusing the second image data feature 20 dimensions and the third image data feature 30 dimensions (color features 10 dimensions, texture feature dimensions, gradient feature 5 dimensions), obtains image classification data features 50 dimensions. In the preferred embodiment, the digestive tract images are classified into esophagus, gastric wall folds, cardia, pylorus, fundus, antrum, angulus, duodenum, jejunum, ileum, cecum, colon and rectum based on the obtained image classification data features.

The key image positioning module 4 processes the classified capsule endoscopic images list, and filters interference in the classified image list. During filtering, it is necessary to continuously adjust the filter parameters until the interference is completely filtered. Then, the key image positioning module 4 searches for the position of the first image of each specific anatomical structure in filtered capsule endoscopic image list.

The key image positioning module 4 processes the classified capsule endoscopic images list to obtain the position of the first image of each specific anatomical structure, so that the physicians can quickly review the images. When searching for key images, the key image positioning module 4 classifies the stomach images (gastric wall folds, cardia, pylorus, gastric fundus, antrum and angulus) into one category. The digestive tract images include more stomach images and intestine images (duodenum, jejunum, ileum, cecum, colon, rectum) but less esophagus images. Different methods are needed to locate the first stomach image and the first intestine image. The specific method to locate the first intestine image is as follows.

Step S41, the position $Pos_f$ of the first intestine image and the position $Pos_l$ of the last intestine image are found in the classified List and, and whether there are other images between $Pos_f$ and $Pos_l$ is confirmed. If there are other images between $Pos_f$ and $Pos_l$, filtering is needed, until there are no other images between $Pos_f$ and $Pos_l$, and $Pos_f$ is the position of the first intestine image.

In the step S41, any filtering method can be used. In the preferred embodiment, the median filtering is used.

During filtering, it is needed to continuously adjust the filter parameters. The specific adjustment method is: set an initial width of filter window, of which, the value range is Win=[3,101], and after each filtering, increase the width of filter window using $Win_i=Win_{i-1}+dWin$, wherein, $Win_i$ represents the width of filter window in the i-th filtering, $Win_{i-1}$ represents the width of filter window in the i−1-th filtering, that is the width of filter window in previous filtering; dWin is the increased value of the filter window width after each filtering, of which, the value range is dWin=[2,500]. In the preferred embodiment, Win=51, dWin=50.

The methods of searching for the key positions of intestine images (duodenum, jejunum, ileum, cecum, colon, rectum) are the same, and the anatomical structures in the intestine images appear in the sequence of duodenum, jejunum, ileum, cecum, colon and rectum, so during processing, the length of the images list to be processed can be continuously adjusted to reduce list interference. The specific method is:

$$Local_{i+1} = find(List(Local_i : T-1)).$$

Wherein, T is the total length of the classified list, $List(Local_i : T-1)$ is a partial list of the List cut from the position $Local_i$ to the position T−1, find( ) represents the process of finding the position where the first key image appears in the step S41, $Local_0=0$, $Local_1$, $Local_2$, $Local_3$, $Local_4$, $Local_5$ and $Local_6$ respectively represent the positions where the first images of duodenum, jejunum, ileum, cecum, colon and rectum appear.

For the position where the first stomach image appears, a different method from that of finding the position where the first intestine image appears is needed, that is, the filter parameters need to be adjusted. The number of esophagus images is less compared to the stomach and intestine images, so it is necessary to reduce the filter window width to prevent the esophagus image from being filtered in the filtering process. The specific method to locate the first stomach image is as follows.

Step S42, the previous classification list List(0: $Local_1$) of intestine images is cut to filter. During filtering, the initial window parameter Win' of filter and the increased value dWin' of the filter window width need to be adjusted. After num filtering, the position of the first stomach image is the key position of the stomach image to be searched.

For the key image position of stomach, the filter window width cannot be too large. Generally, Win'=[3,15], dWin'=[2,10]. In the preferred embodiment, the initial width is Win'=9, the increased value of the filter window width is dWin'=3, and num filtering is performed. The value range of num is [1,5]. In the preferred embodiment, num=3.

The present invention further provides a transfer learning based capsule endoscopic images classification method, comprising the following steps.

Step 1: the image preprocessing module 1 removes the capsule endoscopic images with the average brightness value beyond the preset threshold, and remove the capsule endoscopic images without details based on image brightness standard deviation and image brightness gradient.

Step 2: the similar image removal module 2 removes similar images from the pre-processed capsule endoscopic images using optical flow method.

Step 3: the image classification module 3 classifies the processed capsule endoscopic images through the step 1 and step 2 according to the corresponding anatomical structure, and obtains the classified capsule endoscopic images list arranged in chronological order.

Step 4: the key image positioning module 4 determines and labels the position of the first image of each specific anatomical structure in the classified capsule endoscopic images list arranged in chronological order.

In the transfer learning based capsule endoscopic images classification system disclosed herein, all of other specific methods can be used for capsule endoscopic images classification method, which cannot be repeated here.

Although certain disclosed embodiments of the present disclosure have been specifically described, the present disclosure is not to be construed as being limited thereto. Various changes or modification may be made to the present disclosure without departing from the scope and spirit of the present disclosure.

What is claimed is:

1. A system for transfer learning based capsule endoscopic images classification comprising:
one or more computer processors configured to:
remove acquired capsule endoscopic images with an average brightness value beyond a preset threshold, and remove the capsule endoscopic images without details based on image brightness standard deviation and image brightness gradient;
remove similar images from the capsule endoscopic images using optical flow method;
classify the capsule endoscopic images according to the corresponding anatomical structure to obtain a list of classified capsule endoscopic images arranged in chronological order based on the classified capsule endoscopic images; and
determine and label the position of the first image of each specific anatomical structure in the classified capsule endoscopic images list arranged in chronological order;
wherein
the one or more computer processors are further configured to remove similar images from the capsule endoscopic images using optical flow method, comprising:
setting K feature points in the effective area of the current capsule endoscopic image;
adjusting the brightness of next capsule endoscopic image, and adjusting the average brightness value of the next capsule endoscopic image as the same as the average brightness value of the current capsule endoscopic image;
in the effective area of the said next capsule endoscope image, setting the positions of feature points of the current capsule endoscopic image as initial positions, and searching for the best matching position of each feature point in the current capsule endoscopic image around the initial positions using optical flow method; and
assigning a weight to the best matching position of each feature point, calculating the sum of weights of the best matching positions of all feature points as the image matching weight W, and removing similar images using the image matching weight W;
wherein
when the image matching weight W is less than the image matching weight threshold Wth, or the number of feature points P where the best matching positions are found is less than the threshold Pth, it is determined that the corresponding capsule endoscopic images are not similar, otherwise it is determined that the corresponding capsule endoscopic images are similar;
wherein
when the standard deviation $S_i$ in the neighborhood of the i-th feature point of the current capsule endoscopic image is greater than the threshold AStd for determining whether there are details in the neighborhood, it is determined that there are details in the neighborhood of the i-th feature point, and the matching weight of the i-th feature point is u; otherwise, the matching weight of the i-th feature point is v.

2. The system of claim 1, wherein the one or more computer processors are further configured to calculates an average brightness value M in the effective area of a capsule endoscopic image, wherein when the average brightness value M is less than the too dark threshold Low, the corresponding capsule endoscopic image is determined as too dark and the image is removed; when the average brightness value M is greater than the too bright threshold High, the corresponding capsule endoscopic image is determined as too bright and the image is removed.

3. The system of claim 1, wherein the one or more computer processors are further configured to calculates an image brightness standard deviation S and an image brightness gradient G in the effective area of an capsule endoscopic image, and counts the number of pixels B as the image brightness gradient G meets requirements, wherein when the image brightness standard deviation S is less than the image brightness standard deviation threshold Std or the number of pixels B is less than the threshold for an effective gradient GradNum, the corresponding capsule endoscopic image is determined that it has no details and removes it.

4. The system of claim 1, wherein the K feature points are setting uniformly in the effective area of the current capsule endoscopic image.

5. The system of claim 1, wherein the one or more computer processors are further configured to:
   obtain a first image data feature from the capsule endoscopic images by using a preset image data model;
   obtain a second image data feature from the first image data feature by using a transfer learning model, and at the same time obtain a third image data feature from the capsule endoscopic images by the manual feature extraction; and
   fuse the second image data feature and the third image data feature to obtain an image classification data feature; according to specific anatomical structures, classify the capsule endoscopic images by the image classification data feature.

6. The system of claim 5, wherein the third image data features comprise image color, texture, and gradient features, wherein the image color features are calculated using the Hu matrix of each channel of hue, saturation, value (HSV), and image texture features are calculated using a completed local binary pattern (CLBP) histogram.

7. The system of claim 1, wherein the one or more computer processors are further configured to removes interference data from the classified capsule endoscopic images list arranged in chronological order by filtering, and then search for the position of the first image of each anatomical structure in filtered capsule endoscopic images list.

8. A method for transfer learning based capsule endoscopic images classification, comprising:
   removing acquired capsule endoscopic images with an average brightness value beyond the preset threshold, and removing the capsule endoscopic images without details based on image brightness standard deviation and image brightness gradient;
   removing similar images from the capsule endoscopic images using optical flow method;
   classifying the capsule endoscopic images according to the corresponding anatomical structure to obtain a list the classified capsule endoscopic images list arranged in chronological order based on the classified capsule endoscopic images;
   determining and labeling the position of the first image of each specific anatomical structure in the classified capsule endoscopic images list arranged in chronological order.

9. The method of claim 8, comprising removing the capsule endoscopic images with the average brightness value beyond the preset threshold by:
   calculating an average brightness value M in the effective area of a capsule endoscopic image, wherein when the average brightness value M is less than the too dark threshold Low, determining that the corresponding capsule endoscopic image as too dark and removing the image; when the average brightness value M is greater than the too bright threshold High, determining that the corresponding capsule endoscopic image as too bright and removing the image.

10. The method of claim 8, comprising removing the capsule endoscopic images without details by:
    calculating an image brightness standard deviation S and an image brightness gradient G in the effective area of an capsule endoscopic image, and counting the number of pixels B as the image brightness gradient G meets requirements, wherein when the image brightness standard deviation S is less than the image brightness standard deviation threshold Std or the number of pixels B is less than the threshold for an effective gradient GradNum, determining that the corresponding capsule endoscopic image has no details and removing it.

11. The method of claim 8, comprising removing similar images from the capsule endoscopic images by:
    setting K feature points in the effective area of the current capsule endoscopic image;
    adjusting the brightness of next capsule endoscopic image, and adjusting the average brightness value of the next capsule endoscopic image as the same as the average brightness value of the current capsule endoscopic image;
    in the effective area of the said next capsule endoscope image, setting the positions of feature points of the current capsule endoscopic image as initial positions, and searching for the best matching position of each feature point in the current capsule endoscopic image around the initial positions using optical flow method; and
    assigning a weight to the best matching position of each feature point, calculating the sum of weights of the best matching positions of all feature points as the image matching weight W, and removing similar images using the image matching weight W.

12. The method of claim 11, wherein the K feature points are setting uniformly in the effective area of the current capsule endoscopic image.

13. The method of claim 11, wherein when the image matching weight W is less than the image matching weight threshold Wth, or the number of feature points P where the best matching positions are found is less than the threshold Pth, it is determined that the corresponding capsule endoscopic images are not similar, otherwise it is determined that the corresponding capsule endoscopic images are similar.

14. The method of claim 11, wherein when the standard deviation $S_i$ in the neighborhood of the i-th feature point of the current capsule endoscopic image is greater than the threshold AStd for determining whether there are details in the neighborhood, it is determined that there are details in the neighborhood of the i-th feature point, and the matching weight of the i-th feature point is u; otherwise, the matching weight of the i-th feature point is v.

15. The method of claim 8, comprising classifying the capsule endoscopic images by:
    obtaining a first image data feature from the capsule endoscopic images by using a preset image data model;
    obtaining a second image data feature from the first image data feature by using a transfer learning model, and at the same time obtaining a third image data feature from the capsule endoscopic images by the manual feature extraction; and fusing the second image data feature and the third image data feature to obtain an image classification data feature; according to specific anatomical structures, classifying the capsule endoscopic images by the image classification data feature.

16. The method of claim 15, wherein the third image data features comprise image color, texture, and gradient features, wherein the image color features are calculated using the Hu matrix of each channel of hue, saturation, value (HSV), and image texture features are calculated using a completed local binary pattern (CLBP) histogram.

17. The method of claim 8, comprising determining and labeling the position of the first image by:
removing interference data from the classified capsule endoscopic images list arranged in chronological order by filtering, and then searching for the position of the first image of each anatomical structure in filtered capsule endoscopic images list.

* * * * *